United States Patent
Zhang et al.

(10) Patent No.: US 10,231,973 B2
(45) Date of Patent: *Mar. 19, 2019

(54) SALTS OF QUINAZOLINE DERIVATIVE AND METHOD FOR PREPARING THE SAME

(71) Applicants: CHIA TAI TIANQING PHARMACEUTICAL GROUP CO., LTD., Lianyungang, Jiangsu (CN); CENTAURUS BIOPHARMA CO., LTD., Beijing (CN); LIANYUNGANG RUNZHONG PHARMACEUTICAL CO., LTD., Lianyungang, Jiangsu (CN)

(72) Inventors: Xiquan Zhang, Lianyungang (CN); Song Tang, Lianyungang (CN); Weiwei Feng, Lianyungang (CN); Xin Tian, Lianyungang (CN); Zhilin Chen, Lianyungang (CN); Hongmei Gu, Lianyungang (CN); Hongjiang Xu, Lianyungang (CN); Fei Liu, Lianyungang (CN)

(73) Assignees: Chai Tai Tianqing Pharmaceutical Group Co., Ltd., Lianyungang (CN); CENTAURUS BIOPHARMA CO., LTD., Beijing (CN); LIANYUNGANG RUNZHONG PHARMACEUTICAL CO., LTD., Lianyungang (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/560,099

(22) PCT Filed: Mar. 18, 2016

(86) PCT No.: PCT/CN2016/076693
§ 371 (c)(1),
(2) Date: Sep. 20, 2017

(87) PCT Pub. No.: WO2016/150340
PCT Pub. Date: Sep. 29, 2016

(65) Prior Publication Data
US 2018/0085369 A1    Mar. 29, 2018

(30) Foreign Application Priority Data

Mar. 20, 2015 (CN) .......................... 2015 1 0125962

(51) Int. Cl.
| | |
|---|---|
| *C07D 403/12* | (2006.01) |
| *C07D 405/14* | (2006.01) |
| *C07D 239/94* | (2006.01) |
| *C07D 211/40* | (2006.01) |
| *C07D 401/12* | (2006.01) |
| *A61K 31/517* | (2006.01) |
| *A61K 45/06* | (2006.01) |
| *A61K 31/5377* | (2006.01) |
| *A61K 31/4427* | (2006.01) |

(52) U.S. Cl.
CPC ........ *A61K 31/517* (2013.01); *A61K 31/4427* (2013.01); *A61K 31/5377* (2013.01); *A61K 45/06* (2013.01); *C07D 211/40* (2013.01); *C07D 239/94* (2013.01); *C07D 401/12* (2013.01); *C07D 403/12* (2013.01); *C07D 405/14* (2013.01); *A61K 2300/00* (2013.01)

(58) Field of Classification Search
CPC .. C07D 403/12; C07D 405/14; C07D 239/94; C07D 211/40; C07D 401/12; A61K 31/517; A61K 45/06
See application file for complete search history.

(56) References Cited

U.S. PATENT DOCUMENTS

| | | | |
|---|---|---|---|
| 6,344,455 B1 | 2/2002 | Bridges et al. | |
| 9,725,439 B2* | 8/2017 | Xiao | .......... C07D 403/12 |

(Continued)

FOREIGN PATENT DOCUMENTS

| | | |
|---|---|---|
| AU | 2002219174 B2 | 7/2002 |
| CN | 1882569 A | 12/2006 |

(Continued)

OTHER PUBLICATIONS

Borgatti-et-al., 2017, https://www.ncbi.nlm.nih.gov/pubmed/28193671.*

(Continued)

*Primary Examiner* — Sun Jae Yoo
(74) *Attorney, Agent, or Firm* — Seed IP Law Group LLP

(57) ABSTRACT

The present application relates to maleates of a compound of Formula I, methods for preparing the same, pharmaceutical compositions thereof and uses thereof in the treatment of tumors, such as non-small cell lung cancer, breast cancer, and other malignant tumors.

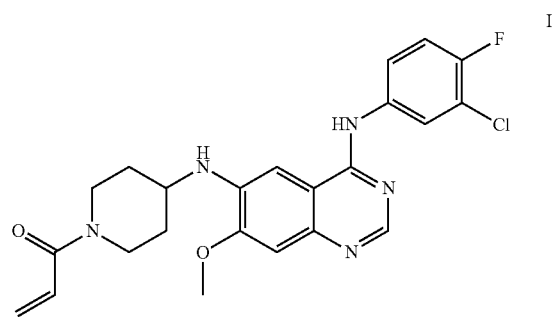

I

14 Claims, No Drawings

(56) References Cited

U.S. PATENT DOCUMENTS

| | | |
|---|---|---|
| 2005/0085495 A1 | 4/2005 | Soyka et al. |
| 2008/0300248 A1 | 12/2008 | Guo et al. |
| 2010/0179120 A1 | 7/2010 | Lee et al. |

FOREIGN PATENT DOCUMENTS

| | | |
|---|---|---|
| CN | 101003514 A | 7/2007 |
| CN | 101679384 A | 3/2010 |
| CN | 101878203 A | 11/2010 |
| CN | 103948689 A | 7/2014 |
| CN | 104513229 A | 4/2015 |
| JP | 2002-530386 A | 9/2002 |
| JP | 2004-516283 A | 6/2004 |
| JP | 2007-510624 A | 4/2007 |
| JP | 2010-529115 A | 8/2010 |
| WO | 00/31048 A1 | 6/2000 |
| WO | 2005/028469 A1 | 3/2005 |
| WO | 2005/037824 A2 | 4/2005 |
| WO | 2007/055513 A1 | 5/2007 |
| WO | 2008/002039 A1 | 1/2008 |
| WO | 2008/150118 A2 | 12/2008 |
| WO | 2009/057139 A2 | 5/2009 |
| WO | 2013/042006 A1 | 3/2013 |
| WO | 2013/051883 A2 | 4/2013 |

OTHER PUBLICATIONS

EGFR, 2017, https://en.wikipedia.org/wiki/Epidermal_growth_factor_receptor.*
Colorectal, 2017, https://www.cancer.org/cancer/colon-rectal-cancer/treating/targeted-therapy.html.*
Faller et al., 2017, https://www.ncbi.nlm.nih.gov/pmc/articles/PMC2747340/.*
Mahmud-et-al., 2017, https://www.ncbi.nlm.nih.gov/pmc/articles/PMC4971659/.*
Cancer-definition, 2017, https://www.cancer.gov/about-cancer/understanding/what-is-cancer.*
Ayyappan et al., Anticancer Research, 33, 4139-4156 (2013).*
International Search Report, dated May 18, 2016, for International Application No. PCT/CN2016/076693, 3 pages.
Sun et al., "The research progress of gefitinib synthesis," *Fine and Specialty Chemicals* 19(5):40-41, 2011. (with English Abstract).
Li et al., "Epidermal growth factor receptor inhibitors: a patent review," Expert Opin. Ther. Patents 24(3):309-321, 2014.

* cited by examiner

SALTS OF QUINAZOLINE DERIVATIVE AND METHOD FOR PREPARING THE SAME

CROSS REFERENCE TO RELATED APPLICATIONS

The present application claims the benefit of Chinese Patent Application No. 201510125962.4 filed with the State Intellectual Property Office of China on Mar. 20, 2015, the contents of which are hereby incorporated herein by reference in their entireties.

TECHNICAL FIELD

The present application relates to the field of pharmaceutical chemistry, and more particularly, to a salt of a quinazoline derivative, a method for preparing the same and a medical use thereof.

BACKGROUND

Epidermal Growth Factor Receptor (EGFR) is a tyrosine kinase receptor, and widely distributed at the surfaces of the mammalian epithelial cells, fibroblasts, glial cells, keratinocytes and so on. EGFR signaling pathway plays an important role in the physiological processes of cells, such as growth, proliferation, differentiation and the like. The functional deficiency of protein tyrosine kinases, such as EGFR, etc., or the abnormality in the activity or cellular localization of key factors in the related signaling pathway, may all cause occurrence of tumors, diabetes, immune deficiencies and cardiovascular diseases.

$N^6$-(1-acryloylazacyclohexan-4-yl)-$N^4$-(3-chloro-4-fluorophenyl)-7-methoxy quinazoline-4,6-diamine has a structure represented by Formula I

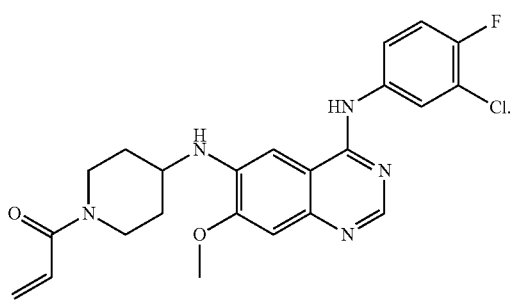

The compound of Formula I is a selective epidermal growth factor receptor inhibitor. It can competitively bind to the phosphorylation site of tyrosine kinase at an intracellular domain to block an interaction between the phosphorylation site and ATP, and thereby inhibit the tyrosine phosphorylation and a series of downstream signal transduction, and then inhibit the growth of tumor cells. The compound of Formula I therefore can be used to treat various malignant tumors, such as non-small cell lung cancer, breast cancer and the like. See Chinese Patent Application No. 201310452885.4, which is hereby incorporated herein by reference in its entirety.

SUMMARY OF THE INVENTION

In one aspect, the present application provides a maleate of a compound of Formula I,

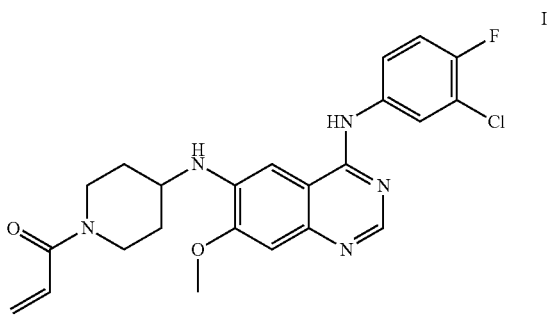 [SMILES: C=CC(=O)N1CCC(Nc2cc3c(Nc4ccc(F)c(Cl)c4)ncnc3cc2OC)CC1]

wherein a molar ratio of maleic acid to the compound of Formula I depends on the amount of maleic acid used in the preparation of said salt. For example, the molar ratio of the compound of Formula I to maleic acid in the maleate may be in a range of 1:0.5-4.

In another aspect, the present application provides a method for preparing a maleate of a compound of Formula I, comprising: (1) preparing a solution of the compound of Formula I; (2) contacting the solution of the compound of Formula I obtained from step (1) with maleic acid; and (3) spray-drying a reaction mixture obtained from step (2) to afford the maleate of the compound of Formula I.

In another aspect, the present application provides a pharmaceutical composition, comprising a maleate of a compound of Formula I and a pharmaceutically acceptable carrier, excipient, diluent and/or vehicle.

In yet another aspect, the present application provides use of a maleate of a compound of Formula I or a pharmaceutical composition thereof in the preparation of a medicament for the treatment of a tumor.

In yet another aspect, the present application provides a method for treating a tumor, comprising administering a maleate of a compound of Formula I or a pharmaceutical composition thereof to a subject in need thereof.

In yet another aspect, the present application provides a maleate of a compound of Formula I or a pharmaceutical composition thereof for use in the treatment of a tumor.

DETAILED DESCRIPTION

In the following description, certain specific details are included to provide a thorough understanding of various disclosed embodiments. However, those skilled in the relevant art will recognize that the embodiments may be practiced with other methods, components, materials, and the like, instead of one or more of these specific details.

Unless the context requires otherwise, throughout the specification and claims thereafter, the term "comprise" and English variations thereof, such as "comprises" and "comprising", are to be construed in an open and inclusive sense, i.e., "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or".

In one aspect, the present application provides a maleate of a compound of Formula I,

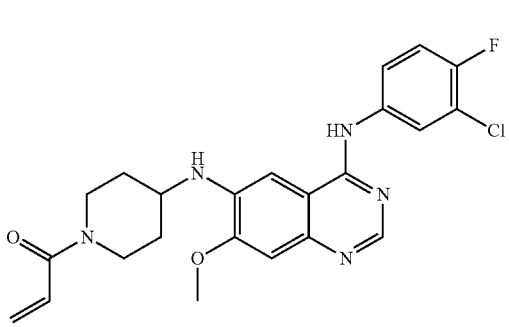

wherein a molar ratio of maleic acid to the compound of Formula I depends on the amount of maleic acid used in the preparation of said salt. For example, the molar ratio of the compound of Formula I to maleic acid in the maleate may be in a range of 1:0.5-4.

In some embodiments of the present application, the molar ratio of the compound of Formula I to maleic acid in the maleate is 1:1. In still other embodiments of the present application, the molar ratio of the compound of Formula I to maleic acid in the maleate is 1:2.

In another aspect, the present application provides a preparation method of a maleate of a compound of Formula I, comprising (1) preparing a solution of a compound of Formula I; (2) mixing the solution of the compound of Formula I obtained from step (1) with maleic acid; and (3) spray-drying a reaction mixture obtained from step (2) to afford the maleate of the compound of Formula I.

In some embodiments, a molar ratio of the amount of the compound of Formula I to that of maleic acid used in the preparation method is in a range of 1:1-20, preferably 1:1-15, and most preferably 1:1-10.

In the step (1) of the preparation method, the compound of Formula I may be dissolved in an organic solvent to prepare a solution of the compound of Formula I. The organic solvent includes all organic solvents capable of dissolving the compound of Formula I, such as DMF.

In the step (2) of the preparation method, the solution of the compound of Formula I obtained from step (1) may be mixed with maleic acid or a solution of maleic acid, and if necessary, the resulting reaction mixture may be heated to a suitable temperature, for example, 60° C. to 100° C., preferably 80° C. In some embodiments, the solution of maleic acid is an organic solution of maleic acid obtained by mixing maleic acid with an organic solvent. In some embodiments of the present application, the organic solvent is, for example, DMF.

In some embodiments, a solvent miscible with the organic solvents used in step (1) and/or step (2), such as water, may be added prior to the spray-drying.

In yet another aspect, the present application provides a pharmaceutical composition comprising a maleate of a compound of Formula I and a pharmaceutically acceptable carrier, excipient, diluent and/or vehicle.

The term "pharmaceutical composition" as used herein refers to a formulation produced by a compound of the present application and a carrier, excipient, diluent and/or vehicle that is generally accepted in the medicine field for the delivery of a bioactive compound to an organism (e.g., human). The purpose of the pharmaceutical composition is to facilitate the administration of the compound of the present application to the organism.

The term "pharmaceutically acceptable carrier" as used herein refers to those carriers and diluents that do not cause significant stimulation to an organism, and will not impair the bioactivity and properties of an active compound. "Pharmaceutically acceptable excipient and/or vehicle" refers to an inert substance that is administered together with an active ingredient and is beneficial to the delivery of the active ingredient to an organism. "Pharmaceutically acceptable carrier, excipient, diluent and/or vehicle" include, but are not limited to, any carriers, excipients, vehicles, glidants, sweetening agents, diluents, preservatives, dyes/colorants, flavoring agents, surfactants, wetting agents, dispersants, disintegrants, suspending agents, stabilizers, isotonic agents, solvents, or emulsifier, and the like, which can be used in human or livestock. Non-limiting examples of an excipient include calcium carbonate, calcium phosphate, various sugars and starches, cellulose derivatives, gelatins, vegetable oils, polyethylene glycols, and the like.

The maleate of the compound of Formula I of the present application may be administered in its pure form or in the form of an appropriate pharmaceutical composition. The pharmaceutical composition of the present application may be prepared by combining the maleate of the compound of Formula I of the present application with an appropriate pharmaceutically acceptable carrier, diluent or excipient, and may be formulated into solid, semi-solid, liquid or gaseous formulations, such as tablets, pills, capsules, powders, granules, ointments, emulsions, suspensions, solutions, suppositories, injections, inhalants, gels, microspheres, aerosols, and the like.

Typical administration routes of the maleate of the compound of Formula I of the present application or the pharmaceutical composition thereof include, but are not limited to, oral, rectal, transmucosal, enteral administration, or local, transdermal, inhalation, parenteral, sublingual intravaginal, intranasal, intraocular, intraperitoneal, intramuscular, subcutaneous, and intravenous administration. The preferred administration route is the oral administration.

The pharmaceutical composition of the present application may be prepared by using a method known to a person skilled in the art, such as a conventional mixing method, dissolution method, granulation method, dragee manufacture method, grinding method, emulsification method, freeze-drying method, and the like.

In a preferred embodiment, the pharmaceutical composition of the present application is in oral form. For oral administration, the pharmaceutical composition may be formulated by mixing the active compound with a pharmaceutically acceptable carrier, excipient, diluent and/or vehicle well-known in the art. These carriers, excipients, diluents and/or vehicles enable the pharmaceutical composition of the present application to be formulated into tablets, pills, lozenges, dragees, capsules, liquids, gels, syrups, suspensions, and the like, for oral administration to a patient. A solid oral composition may be prepared by a conventional mixing, filling or tabletting method.

During said administration, a dosage of the maleate of the compound of Formula I is preferably 0.01-200 mg/kg body weight per day.

In yet another aspect, the present application provides use of a maleate of a compound of Formula I or a pharmaceutical composition thereof in the preparation of a medicament for the treatment of a tumor.

In yet another aspect, the present application provides a method for treating a tumor, comprising administering a maleate of a compound of Formula I or a pharmaceutical composition thereof to a subject in need thereof.

In yet another aspect, the present application provides a maleate of a compound of Formula I or a pharmaceutical composition thereof for use in the treatment of a tumor.

In some embodiments, the tumor includes, but is not limited to, non-small cell lung cancer and breast cancer.

EXAMPLES

Example 1 Preparation of a Compound of Formula I

Step 1: 4-chloro-7-fluoro-6-nitroquinazoline

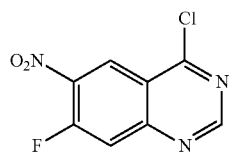 [SMILES: O=[N+]([O-])c1cc2c(Cl)ncnc2cc1F]

7-fluoro-6-nitroquinazoline-4(3H)-one (2.0 g, 9.6 mmol) and one drop of N,N-dimethylformamide were refluxed overnight in thionyl chloride (6 mL), and then the reaction mixture was concentrated in vacuo. To the residue was added toluene, and then concentrated in vacuo again to remove the remaining thionyl chloride. The title compound (2 g, 92%) was obtained.

$^1$H NMR (CDCl$_3$): δ 9.18 (1H, s), 9.05 (1H, d, J=7.6 Hz), 7.95 (1H, d, J=10.4).

Step 2:
3-chloro-N-(3,4-dimethoxybenzyl)-4-fluoroaniline

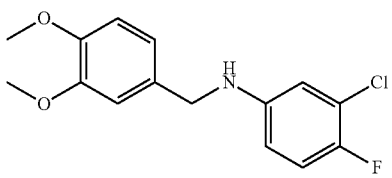 [SMILES: COc1ccc(CNc2ccc(F)c(Cl)c2)cc1OC]

To 1,2-dichloroethane (30 mL) were added 3-chloro-4-fluoroaniline (2.9 g, 20 mmol) and 3,4-dimethoxybenzaldehyde (3.3 g, 20 mmol), and stirred at room temperature for 1 hour. Then, sodium triacetoxyborohydride (10 g, 50 mmol) was added, and the reaction mixture was stirred at room temperature overnight. The reaction mixture was poured into 100 mL of water, and extracted with dichloromethane. The organic phase was separated, washed with saturated brine, dried over anhydrous sodium sulfate, and concentrated in vacuo to afford the title compound (5.5 g, 93%).

$^1$H NMR (CDCl$_3$): δ 6.94-6.82 (4H, m), 6.63-6.61 (1H, m), 6.45-6.41 (1H, m), 4.18 (2H, s), 3.98 (1H, br), 3.87 (3H, s), 3.86 (3H, s).

Step 3: N-(3-chloro-4-fluorophenyl)-N-(3,4-dimethoxybenzyl)-7-fluoro-6-nitroquinazoline-4-amine

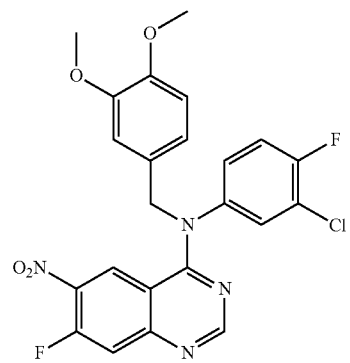 [SMILES: COc1ccc(CN(c2ccc(F)c(Cl)c2)c2ncnc3cc(F)c([N+](=O)[O-])cc23)cc1OC]

To acetonitrile (20 mL) were added 4-chloro-7-fluoro-6-nitroquinazoline (2.1 g, 9.2 mmol) and 3-chloro-N-(3,4-dimethoxybenzyl)-4-fluoroaniline (2.7 g, 9.2 mmol), and refluxed for 3 hours. After cooling, the reaction mixture was neutralized with sodium carbonate solution, and extracted with ethyl acetate. The organic phase was separated, washed with saturated brine, dried over anhydrous sodium sulfate, and concentrated in vacuo to afford the title compound (3.6 g, 80%).

Step 4: N-(3-chloro-4-fluorophenyl)-N-(3,4-dimethoxybenzyl)-7-methoxy-6-nitroquinazoline-4-amine

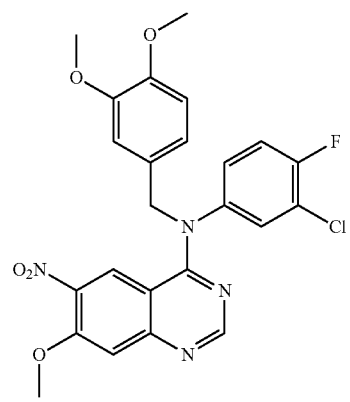 [SMILES: COc1ccc(CN(c2ccc(F)c(Cl)c2)c2ncnc3cc(OC)c([N+](=O)[O-])cc23)cc1OC]

Metallic sodium (113 mg, 5.0 mmol) was added to anhydrous methanol (20 mL), and stirred at room temperature for 10 minutes. N-(3-chloro-4-fluorophenyl)-N-(3,4-dimethoxybenzyl)-7-fluoro-6-nitroquinazoline-4-amine (2.4 g, 5.0 mmol) was then added, and the resulting reaction mixture was stirred at 40° C. for 6 hours. After cooling, the mixture was poured into 100 mL of water, and extracted with ethyl acetate. The organic phase was washed with saturated brine, dried over anhydrous sodium sulfate, and concentrated in vacuo to afford the title compound (2.35 g, 94%).

$^1$H NMR (CDCl$_3$): δ 8.85 (1H, s), 7.57 (1H, s), 7.35 (1H, s), 7.23-7.19 (2H, m), 7.00-6.96 (1H, m), 6.84-6.78 (2H, m), 5.35 (2H, s), 4.05 (3H, s), 3.88 (3H, s), 3.83 (3H, s).

Step 5: N$^4$-(3-chloro-4-fluorophenyl)-N$^4$-(3,4-dimethoxybenzyl)-7-methoxyquinazoline-4,6-diamine

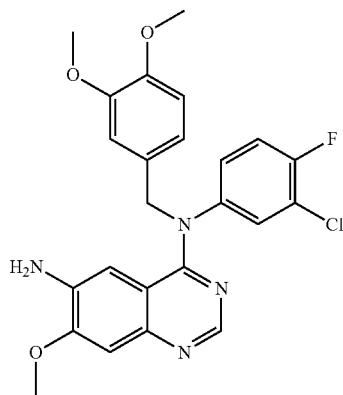

N-(3-chloro-4-fluorophenyl)-N-(3,4-dimethoxybenzyl)-7-methoxy-6-nitroqui-nazoline-4-amine (2.35 g, 4.7 mmol) and Raney nickel (about 0.5 g) were added to tetrahydrofuran (100 mL). The atmosphere was replaced with hydrogen gas, and the reaction mixture was stirred overnight at room temperature under a hydrogen atmosphere (1 atm). The mixture was filtered, and the filtrate was concentrated in vacuo to afford the title compound (2 g, 90%).

Step 6: tert-butyl 4-{{4-[(3-chloro-4-fluorophenyl)(3,4-dimethoxybenzyl)amino]-7-methoxyquinazolin-6-yl}amino}piperidine-1-carboxylate

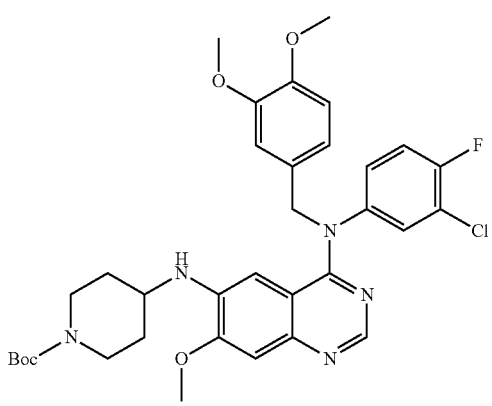 [SMILES: COc1cc2ncnc(N(Cc3ccc(OC)c(OC)c3)c3ccc(F)c(Cl)c3)c2cc1NC1CCN(C(=O)OC(C)(C)C)CC1]

A solution of N$^4$-(3-chloro-4-fluorophenyl)-N$^4$-(3,4-dimethoxy-benzyl)-7-methoxyquinazoline-4,6-diamine (469 mg, 1.0 mmol) and tert-butyl 4-oxopiperidine-1-carboxylate (239 mg, 1.2 mmol) in acetic acid (10 mL) was stirred at room temperature for 2 hours, and then sodium triacetoxyborohydride (254 mg, 1.2 mmol) was added thereto in one portion. After reacting for half an hour, the reaction was quenched by slowly adding water, and extracted with ethyl acetate. The resulting organic phase was washed sequentially with water, 5% NaHCO$_3$ aqueous solution and saturated brine, dried over anhydrous sodium sulfate, and concentrated in vacuo. The residue was separated through silica gel column chromatography to afford the title compound (404 mg, 62%).

Step 7: N$^6$-(piperidin-4-yl)-N$^4$-(3-chloro-4-fluorophenyl)-7-methoxyquinazoline-4,6-diamine

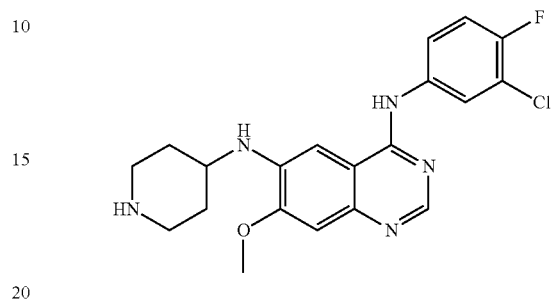

A solution of tert-butyl 4-{{4-[(3-chloro-4-fluorophenyl)(3,4-dimethoxy-benzyl)amino]-7-methoxyquinazolin-6-yl}amino}piperidine-1-carboxylate (0.4 g, 0.61 mmol) in trifluoroacetic acid (8 mL) was stirred at 70° C. for 6 hours. Once the reaction was completed, the reaction mixture was cooled, and concentrated in vacuo. The residue was slurried with ethyl acetate, and filtered to afford a trifluoroacetate of the title compound (0.26 g, 83%).

Step 8: N$^6$-(1-acryloylpiperidin-4-yl)-N$^4$-(3-chloro-4-fluorophenyl)-7-methoxyquinazoline-4,6-diamine

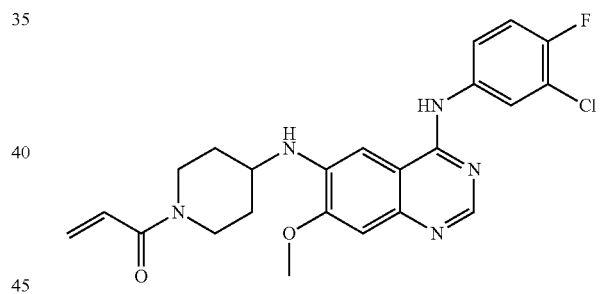

A solution of N$^6$-(piperidin-4-yl)-N$^4$-(3-chloro-4-fluorophenyl)-7-methoxy-quinazoline-4,6-diamine mono-trifluoroacetate (258 mg, 0.5 mmol) and triethylamine (202 mg, 2.0 mmol) in tetrahydrofuran (10 mL) was stirred at room temperature for 30 minutes. After cooling to 0° C., a solution of acryloyl chloride (54 mg, 0.6 mmol) in tetrahydrofuran (2 mL) was added dropwise, and then the reaction was continued for another 30 minutes. The reaction was completed, quenched by slowly adding 5% NaHCO$_3$ solution, and extracted with ethyl acetate. The resulting organic phase was washed with saturated brine, dried over anhydrous sodium sulfate, and concentrated in vacuo. The residue was separated through silica gel column chromatography to afford the target product (150 mg, 66%).

$^1$H NMR (DMSO-d6): δ 9.24 (1H, s), 8.33 (1H, s), 8.09-8.08 (1H, m), 7.77-7.74 (1H, m), 7.42-7.40 (1H, m), 7.23 (1H, s), 7.06 (1H, s), 6.85-6.81 (1H, m), 6.10-6.06 (1H, m), 5.66-5.64 (1H, m), 5.32-5.29 (1H, m), 4.41-4.38 (1H, m), 4.09-4.06 (1H, m), 3.93 (3H, s), 3.79-3.78 (1H, m), 3.35-3.34 (1H, m), 2.87-2.84 (1H, m), 2.03-2.01 (2H, m), 1.44-1.41 (2H, m).

Example 2 Preparation of a Maleate of a Compound of Formula I 5 g of the compound of Formula I was dissolved in 100 mL of DMF at room temperature, and stirred continuously until a homogeneous solution was obtained. 6.3 g of maleic acid was added thereto, and then heated to 80° C. and reacted for 2 h. Then, 100 ml of water was added at this temperature, and the mixture was directly spray-dried to afford 4.0 g of yellow solid powder. The XRD spectrum showed that the powder was an amorphous maleate of the compound of Formula I (1:1).

Example 3 Preparation of a Citrate, Oxalate and Acetate of the Compound of Formula I The citrate, oxalate and acetate of the compound of Formula I were respectively prepared in the same manner as Example 2.

Example 4 Bioavailability Test

Study procedure: Fifteen beagle dogs (7.4~9.4 kg body weight) were randomly divided into 5 groups, and administered orally suspensions of the compound of Formula I, the maleate, citrate, oxalate and acetate thereof (calculated according to the amount of the compound of Formula I) in CMC-Na (carboxymethylcellulose sodium) at a dosage of 5 mg/kg body weight, respectively. Blood samples were taken before and after administration (0.25, 0.5, 1, 2, 4, 6, 8, 12, 24, and 48 h time points), and the concentration of the compound of Formula I for each plasma sample was determined by LC-MS, and then the bioavailability was calculated.

Detection Procedure:

Chromatographic conditions: methanol as mobile phase A and a 0.1% (v/v) aqueous solution of formic acid as mobile phase B, an isocratic elution A:B=52:48; 0.2 mL/min of a flow rate; 35° C. of column temperature; and SHIMADZU Shim-pack VP-ODS $C_{18}$ (5.0 μm, 150 mm×2.0 mm I.D., Shimadzu Corporation) as chromatographic column.

Mass spectrometry conditions: ion source: ESI ionization source, scanning in SIM mode, 250° C. of curved desolventizer (CDL) temperature, 200° C. of heating block temperature; 25V of CDL voltage; +1.60 kV of detection voltage; 1.5 L/min of atomization gas flow rate; 2.0 L/min of dry gas flow rate.

Study Results:

|  | Compound of Formula I | Maleate | Citrate | Oxalate | Acetate |
|---|---|---|---|---|---|
| $C_{max}$ (μg/mL) | 2.82 ± 2.83 | 8.14 ± 0.12 | 1.29 ± 0.37 | 3.59 ± 1.67 | 2.08 ± 0.52 |
| $T_{max}$ (h) | 3.17 ± 4.19 | 1.17 ± 0.76 | 1.33 ± 0.58 | 1.50 ± 0.71 | 3.33 ± 1.15 |
| $T_{1/2}$ (h) | 5.13 ± 2.85 | 5.44 ± 0.72 | 4.48 ± 1.14 | 9.38 ± 4.03 | 9.41 ± 7.90 |
| $AUC_{0-t}$ (μg*h/mL) | 42.14 ± 55.12 | 85.13 ± 25.27 | 10.76 ± 6.55 | 53.20 ± 35.05 | 20.35 ± 0.46 |
| $V_d/F$ (L/kg) | 0.78 ± 1.08 | 0.06 ± 0.02 | 0.61 ± 0.39 | 0.12 ± 0.08 | 0.25 ± 0.01 |
| CL/F (L/h/kg) | 4.67 ± 6.67 | 0.48 ± 0.12 | 4.32 ± 3.79 | 1.39 ± 0.37 | 3.31 ± 2.73 |

Example 5 In Vitro Activity Test

1. Method for In Vitro Enzymology Test

EGFR, EGFR (T790M, L858R), and HER2 kinase were expressed and purified through an insect cell expression system, or purchased from commercially available products.

A platform for testing the kinase activities of EGFR, EGFR (T790M, L858R) and HER2 was established based on Homogeneous Time-Resolved Fluorescence (HTRF) method provided by Cisbio Bioassays, and the activity of the compound was determined with the platform. The compound was diluted at a 3-fold gradient with 100% DMSO, starting from 100 nM (EGFR and HER2) and 1 μM (EGFR-T790M/L858R), respectively. For each concentration, 4 μL of solution was taken and added to 96 μL of reaction buffer (50 mM 4-hydroxyethylpiperazineethanesulfonic acid (HEPES) (pH 7.0), 0.02% $NaN_3$, 0.01% bovine serum albumin (BSA), 0.1 mM Sodium Orthovanadate, 5 mM $MgCl_2$, 50 nM SEB (Cisbio, Cat No.: 61SEBALB), 1 mM DTT). 2.5 μL of the mixture was taken and added to a 384-well plate (OptiPlate-384, PerkinElmer), and then 2.5 μL of the kinase was added, and mixed uniformly through centrifuge. Then, 5 μL of ATP and TK Substrate-biotin was added thereto to initiate the reaction. After the 384-well plate was incubated in an incubator at 23° C. for a certain period of time, the reaction was stopped by adding 5 μL of $Eu^{3+}$-Cryptate labeled TK-Antibody and 5 μL of streptavidin-XL665. The fluorescence values were read on Envision (PerkinElmer) after incubation for 1 hour in the incubator. The $IC_{50}$ values of the compound were calculated using the GraphPad Prism 5.0 software.

2. Anchorage-Independent Cell Proliferation Assay

NCI-H1975, a human non-small cell lung cancer cell, and BT474, a human breast cancer cell line, were cultured in RPIM-1640 or DMEM culture medium supplemented with 10% fetal bovine serum (FBS) in a cell incubator (37° C., 5% $CO_2$). In the test of the compound, culture plates were pre-coated with 0.6% medium, and the cells were resuspended with 0.3% low-melting-point agarose, and then seeded in a 96-well plate at a density of 10,000 cells per well (100 μL). The compound was diluted at a 3-fold gradient, starting from 10 mM. For each of concentration, 2 μL of the solution was taken, and added to 98 μL of culture medium, and then 5.3 μL of the mixture was added to the cell culture medium (0.1% of DMSO final concentration, v/v). After the treatment for one week (7 days), 20 μL of CellTiter-Blue® (Promega) reagent was added, and incubated at 37° C. for 4 hours. Fluorescence signals were read on Envison (Perkin Elmer), and $IC_{50}$ values of the compound for inhibiting cell proliferation were calculated using GraphPad Prism 5.0.

Biological Activity

|  | Enzyme activity ($IC_{50}$ nM) | | | Cell activity ($IC_{50}$ nM) | |
|---|---|---|---|---|---|
| Compound | EGFR | EGFR-L858R/T790M | HER2 | H1975 | BT474 |
| Example 1 | 0.2 | 2.0 | 0.2 | 14.0 | 2.1 |

The invention claimed is:
1. A maleate of a compound of Formula I,

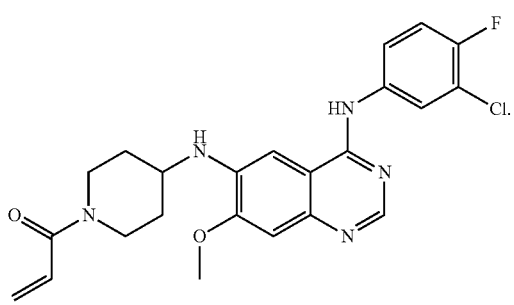

2. The maleate of the compound of Formula I according to claim 1, wherein a molar ratio of the compound of Formula I to maleic acid is 1:0.5-4.
3. The maleate of the compound of Formula I according to claim 2, wherein the molar ratio of the compound of Formula I to maleic acid is 1:1 or 1:2.
4. A method for preparing a maleate of a compound of Formula I:

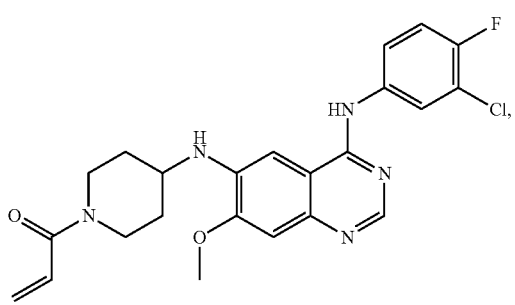

the method comprising: (1) preparing a solution of the compound of Formula I; (2) mixing the solution of the compound of Formula I obtained from step (1) with maleic acid to provide a reaction mixture; and (3) spray-drying the reaction mixture obtained from step (2) to obtain the maleate of the compound of Formula I.
5. The method according to claim 4, wherein a molar ratio of the amount of the compound of Formula I to that of maleic acid in the reaction mixture is 1:1-20.
6. The method according to claim 4, wherein in step (1), the compound of Formula I is dissolved in an organic solvent to prepare the solution of the compound of Formula I.
7. The method according to claim 6, wherein a solvent miscible with the organic solvent is added prior to the spray-drying.
8. A pharmaceutical composition, comprising the maleate of the compound of Formula I according to claim 1, and a pharmaceutically acceptable carrier, excipient, diluent and/or vehicle.
9. A method for treating non-small cell lung cancer or breast cancer, comprising administering the maleate of the compound of Formula I according to claim 1 to a subject in need thereof.
10. A method for treating non-small cell lung cancer or breast cancer, comprising administering the pharmaceutical composition according to claim 8 to a subject in need thereof.
11. The method according to claim 4, wherein a molar ratio of the amount of the compound of Formula I to that of maleic acid in the reaction mixture is 1:1-15.
12. The method according to claim 4, wherein a molar ratio of the amount of the compound of Formula I to that of maleic acid in the reaction mixture is 1:1-10.
13. The method according to claim 6, wherein the organic solvent is DMF.
14. The method according to claim 7, wherein the solvent miscible with the organic solvent is water.

* * * * *